US008652044B2

United States Patent
Abramov

(10) Patent No.: US 8,652,044 B2
(45) Date of Patent: Feb. 18, 2014

(54) PORTABLE NON-CONTACT TONOMETER AND METHOD OF DETERMINING INTRA-OCULAR PRESSURE USING SUCH

(76) Inventor: Igor Abramov, Oceanside, CA (US)

(*) Notice: Subject to any disclaimer, the term of this patent is extended or adjusted under 35 U.S.C. 154(b) by 1216 days.

(21) Appl. No.: 12/506,263

(22) Filed: Jul. 21, 2009

(65) Prior Publication Data

US 2010/0030056 A1 Feb. 4, 2010

Related U.S. Application Data

(60) Provisional application No. 61/085,421, filed on Aug. 1, 2008.

(51) Int. Cl.
*A61B 3/16* (2006.01)
*A61B 3/14* (2006.01)
*A61B 3/10* (2006.01)

(52) U.S. Cl.
USPC ........... 600/401; 600/398; 351/206; 351/208; 351/209; 351/211; 351/212

(58) Field of Classification Search
USPC .......... 600/398, 401; 351/206, 208, 209, 211, 351/212
See application file for complete search history.

(56) References Cited

U.S. PATENT DOCUMENTS

| 5,299,573 | A | 4/1994 | Kobayashi |
| 5,629,747 | A | 5/1997 | Miyake |
| 5,947,898 | A * | 9/1999 | Suzuki et al. ................. 600/405 |
| 6,361,495 | B1 | 3/2002 | Grolman |
| 6,537,215 | B2 | 3/2003 | Miwa |
| 6,623,429 | B2 | 9/2003 | Percival et al. |
| 7,101,335 | B2 * | 9/2006 | Miwa et al. .................... 600/401 |

* cited by examiner

*Primary Examiner* — Jeffrey G Hoekstra
*Assistant Examiner* — Devin Henson

(57) ABSTRACT

A portable non-contact tonometer (2) for measuring Intra-Ocular Pressure (IOP) of subject's eye is presented. Tonometer (2) is designed to be operated by the subject himself. It is housed in a hand-held case (4) which contains compressed air source (40), eye alignment detectors (12, 14), cornea applanation detector system (8, 10), a pressure sensor (32) and optical system for presenting gaze target (48). The animated gaze target (48) advantageously draws subject's attention to itself and keeps his eye (62) in alignment long enough for the measurement to take place, while optionally displaying system status and operating instructions. An audio annunciation system (16) guides the subject in the operation of the tonometer and prepares him for the actual procedure. The timing of the air puff is randomized to prevent subject's conditioning. The overall operation of the tonometer is controlled by a built-in microprocessor (50) system. A 3-D map of cornea is computed and a technique to compute the IOP derived from the difference of 3-D corneal maps before and during the air puff application is disclosed.

19 Claims, 14 Drawing Sheets

PORTABLE NON-CONTACT TONOMETER AND METHOD OF DETERMINING INTRA-OCULAR PRESSURE USING SUCH

CROSS-REFERENCE TO RELATED APPLICATION

This application claims the benefit of Provisional Patent Application Ser. No. 61/085,421 filed 2008 Aug. 1

FIELD OF INVENTION

This invention relates in general to tonometers, and in particular to portable tonometers which can be easily moved and utilized in various positions by subjects themselves or by operators.

BACKGROUND OF INVENTION

Measurement of intra-ocular pressure (IOP) is an important procedure in diagnosing various diseases and abnormalities of the eye as well as monitoring status of ophthalmic therapies and procedures.

IOP is measured by a device called tonometer. Traditional stationary tonometers are used only in an ophthalmologist's office environment and only in a vertical position. There are two basic types of tonometers: the Goldmann-type which has been a universally recognized standard instrument which relies on the direct contact with a subject's cornea, and contact-less tonometers which use a puff of air to achieve flattening or "applanation" of the cornea and then compute the IOP as a function of the air pressure required for such corneal applanation.

Contact tonometers require anesthesia of subject's cornea and carry a potential risk of transmitting eye infection from one subject to another and also a potential damage to the cornea itself if the device is not applied correctly or is improperly calibrated or maintained.

Both of these types of tonometers are quite large and heavy, up to 40 lbs (18 kg) as is in case of the Topcon CT-80 computerized tonometer made by Latham & Philips Ophthalmic Products, Inc. They are therefore consigned to medical offices. They also generally operate only in vertical position and require subjects to be cooperative while a measurement is performed. One non-contact tonometer, Pulsair EasyEye by Keeler, Inc. has a movable measuring head connected to a stationary base, which limits the range of its deployment and utility.

Another type is a contact tonometer which measures IOP by compressing the subject's cornea through the eyelid. One such tonometer made by the Tonopen, Inc. is portable but requires considerable skill for its use to achieve repeatable and reliable readings. The same can be said for the Diaton tonometer marketed by BiCom, Inc. These tonometers require several readings to be taken and then averaged due to the variability of the measurement process.

Measurement of IOP in different subject's positions sometimes results in differing readings, so some medical practitioners suggest measuring it at several different positions.

Uncooperative subjects such as small children have to be sedated in order to perform an IOP measurement. In case of the elderly or in an emergency room setting there's also a need to measure IOP when the subject is prone.

It has been recommended for some cases for the IOP measurements to be performed more or less continuously, as IOP displays diurnal variation which may not be adequately captured and evaluated when a patient has to visit a medical office for an IOP measurement.

It is desirable, therefore to have a means to measure, store and transmit IOP readings remotely, possibly several times a day, without a visit to the doctor's office, while at the same time providing information to the patient.

It is also desirable to have a portable tonometer which can be easily transported and used at subject's home, a tonometer which would be also easy to use both by non-specialist personnel and subjects themselves.

It is also desirable for a tonometer to operate in any position and be usable with pediatric and geriatric patients and other 'difficult' subjects, like those encountered in veterinary practice, without anesthesia or constraints.

OBJECTIVES OF THE INVENTION

Thus, it is an objective of instant invention to provide a portable tonometer which can be easily carried by or to the subject.

Another objective of instant invention is to provide a tonometer which is easy to use, so it can be operated by subject himself, in a home environment rather than by a medical specialist in a medical office.

Yet another objective of instant invention is to provide a tonometer that can be used with pediatric subjects with minimum preparation of the subject or operator training.

Another objective of instant invention is to provide a tonometer which can be used in any position.

Another objective of instant invention is to provide a tonometer which will cause minimized discomfort to the subject during the measurement.

Yet another objective of instant invention is to provide a tonometer that is relatively inexpensive.

Another objective of instant invention is to provide a tonometer which can store and transfer IOP readings to remote devices and locations.

SUMMARY OF THE INVENTION

In accordance with the present invention a self-contained hand-held tonometer is introduced. It is small, lightweight and is preferably battery-operated. The tonometer can be operated by subject himself or an operator. The tonometer operation is essentially automatic and starts upon subject's or operator's turning it on. The tonometer has an internal compressed air generator, either in the form of an electrical pump similar to the ones found in portable blood pressure monitors, or a spring-loaded or electrically actuated plunger moving within a cylinder.

The tonometer employs an internal electronic target display device which is capable of displaying still or moving target image or images along with system information to help align the eye along the optical axis of the tonometer. Such a display can be based on a liquid crystal (LCD), light-emitting diodes (LED's) or other display technologies. In addition, tonometer contains an automatic eye alignment detection subsystem, a pressure sensor, an air puff trigger mechanism, and a corneal applanation detection subsystem.

As an option, the tonometer also has an audio annunciation subsystem to guide user in tonometer operation and also to help acquire and maintain the gaze of the pediatric subjects.

The tonometer contains as an option a deployable forehead rest assembly which further assists with the proper alignment of the subject's eye with respect to the tonometer.

During tonometer operation the subject is urged to look at the target and as soon as his eye is aligned with the optical axis of the device and is at the proper distance, a puff of air is released towards the subject's cornea to achieve its applanation. The timing of air pulse is randomized to minimize a chance of subject's conditioning. The eye alignment detection system consists of one or more optical emitter-detector pairs. A gaze target imaging system limits the field of view of the target display to facilitate proper alignment of the subject's eye. The overall operation of the tonometer is controlled by a built-in microprocessor system.

A variation of the tonometer contains a viewing port and a system status display for an operator-assisted operation.

A yet another variation of the tonometer contains a small video camera pointed toward the subject's eye and a display on the obverse side of the tonometer case. The camera captures the position of the subject's eye which is then shown on the display with optional alignment marks and alignment instructions derived from eye alignment detection system and generated by a microprocessor system. This feature is useful when the tonometer is operated by a person other than the subject himself.

The use of imaging camera enables precision optical techniques to be utilized to measure the degree of corneal applanation. In alternative tonometer embodiment, a reference geometric pattern such as concentric rings or a rectangular grid are projected onto the cornea. The 3-D corneal shape is then calculated from the resulting image, and from the change of the corneal shape in response to an air puff the degree of corneal applanation is computed.

In a yet another variation the tonometer contains internal memory to store IOP readings with a real-time clock function to reference them and an output capability to transmit IOP readings and preferably its self-diagnostic and/or calibration information to a remote devices such as computers, printers or PDAs (personal digital assistants). Such capability can be realized through a wired connection such as a USB or an Ethernet port, or wireless such as radio frequency or infra-red light. These data transmission methods are well known in their respective arts.

PRIOR ART

Prior art contains several contact-less tonometers, some of which are portable. Most of the tonometers of the prior art are designed to be operated by a person other than the subject and require extensive training prior to operation. In contrast, the present tonometer is expressly designed to be operated by subjects themselves, except in some special cases such as the elderly, special patients (immobile, psychiatric, etc.), and children.

The U.S. Pat. No. 6,623,429 to Percival at al. described a hand-held tonometer designed to be used by a trained operator.

None of the prior art tonometers has a moving, animated or picture-like target display to help align subject's eye.

None of the prior art has an audio subsystem to facilitate operation, measurement and to ease subject's possible anxiety.

Likewise, none of the prior art teaches an imaging system restricting the field of view of the alignment target to facilitate alignment.

None of the prior art has a randomized air pulse timing.

Also, none of the prior art teaches a technique to compute the IOP derived from the difference of 3-D corneal maps before and after the air puff application.

OBJECTS AND ADVANTAGES

In contrast to the prior art mentioned hereinabove, the present invention provides a simplified alignment to the subject's eye, which enables operation of the tonometer by subjects themselves, or in case of pediatric subjects, greatly simplifying the procedure, so that even an inexperienced operator, such as child's parent can easily measure subject's IOP.

In addition, the operation of the tonometer is for the most part automatic, further simplifying its operation.

The animated target advantageously draws subject's attention and thus aligns his eye, while optionally displaying system status and operating instructions. In addition, the audio annunciation system guides the subject in the operation of the tonometer and prepares him for the actual procedure.

For pediatric subjects the audio annunciation system calms them prior to the measurement, encourages them to look at the target image and praises them after the measurement is complete. Preferably animated images of the popular cartoon characters or objects are displayed to draw subject's attention and to fixate his gaze in proper alignment and for sufficient time for a reliable measurement to be taken. For example, an animated image of a dragon puffing smoke can be displayed in preparation for the air puff of the tonometer. The subject's anxiety is diminished as the procedure is presented as a type of play. This additionally reduces the so-called 'squint-squeeze'-induced IOP measurement error.

DESCRIPTION OF THE PREFERRED EMBODIMENT

In the foregoing description like components are referenced by the like numerals.

Optical elements and subsystems are presented in simplified form to convey their overall function, such as imaging, collimation, etc. The actual construction and layout of the optical systems and lens elements themselves may differ from their representation and will be governed by the physical optical design considerations. For example, additional folding mirrors and beamsplitters may have to be utilized in order to conform the design within physical constraints of the overall tonometer system, lens elements themselves may have to contain several groups to adapt to system's physical size constraints and control optical aberrations.

Figure 1:
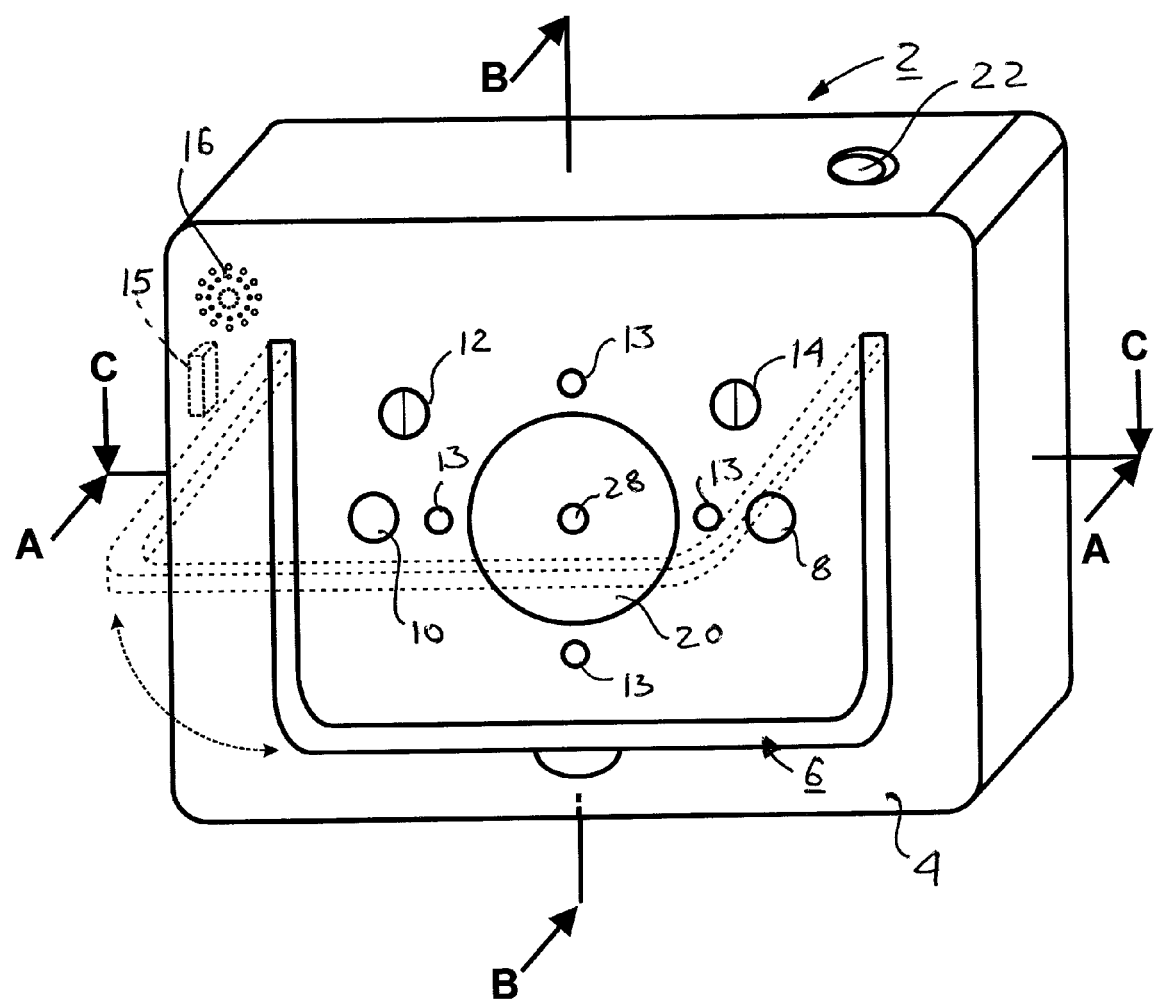
FIG. 1 is a perspective view of the preferred embodiment of the present invention.

The preferred embodiment 2 of the present invention is shown on FIG. 1. Tonometer 2 is housed in housing 4. Referring to FIG. 2, tonometer is controlled by a microprocessor 50 and is powered by an internal power source 52, which can be rechargeable or non-rechargeable battery. The back of the tonometer is shown on FIG. 1A, with the operator observation port 26, data port 15, optional auxiliary display 23, and mode selection buttons 17 visible.

The IOP measurement operation is initiated when subject himself or an operator presses the power button 22 which starts tonometer microprocessor system, and then selects the mode of tonometer operation, such as the measurement to be self-conducted by the subject, pediatric, audio enunciation, gaze target selection, etc. via buttons 17. For instance, for the self-conducted measurement, gaze target 48 includes in addition to the central gaze target system status and alignment information on its periphery. For pediatric use, selection of animated targets can be offered along with a selection of audio accompaniment and/or narration.

Upon the signal from button 22 microprocessor 50 initiates the measurement sequence and controls it to completion.

Pressurization of Air Source

Referring to FIG. 2, microprocessor 50 communicates with and controls system components via bus 51. Under microprocessor 50 control air pump 40 compresses air via a one-way valve 37 in accumulator chamber 36 whose outlet is held closed by electrically-activated valve 34. The air pressure in chamber 36 is monitored by pressure switch 33 which is activated when pressure reaches a pre-determined value. The pump 40 is then stopped and the system status updated accordingly.

Figure 3:
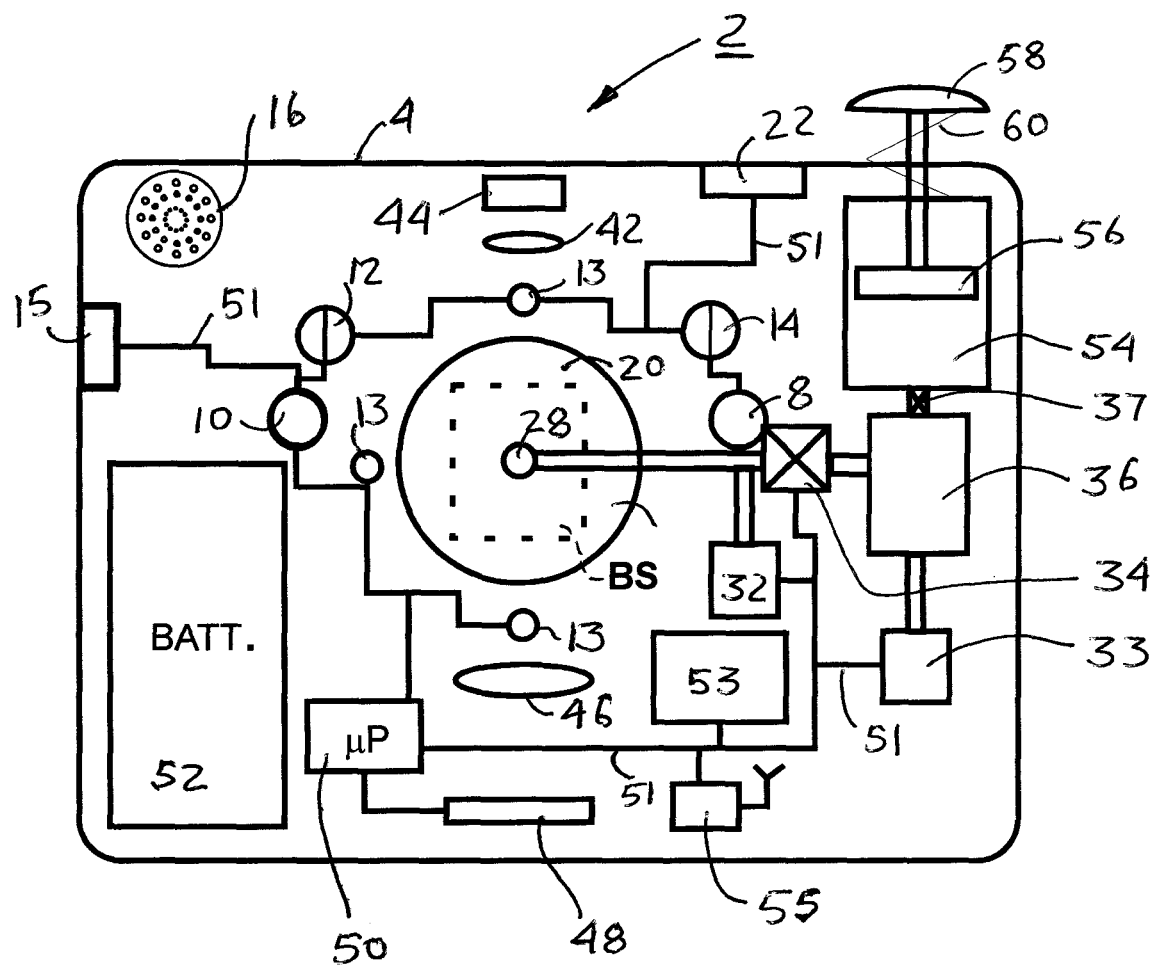
FIG. 3 is a sectional view similar to the embodiment in FIG. 2 but featuring alternative compressed air system

Alternatively, as shown on FIG. 3 electrical air pump can be substituted by a manually operated plunger 56 which compresses air in the chamber 54 which communicates via a one-way valve 37 with accumulator chamber 36. Subject or operator pumps up the air by depressing knob 58 connected to plunger 56. Plunger 56 is returned to its initial position by spring 60. Pressure in chamber 36 is monitored by pressure switch 33 which communicates with microprocessor 50 which in turn generates corresponding notification via an audio signal and/or system status display update when the operating air pressure is achieved.

Alignment

Figure 1A:
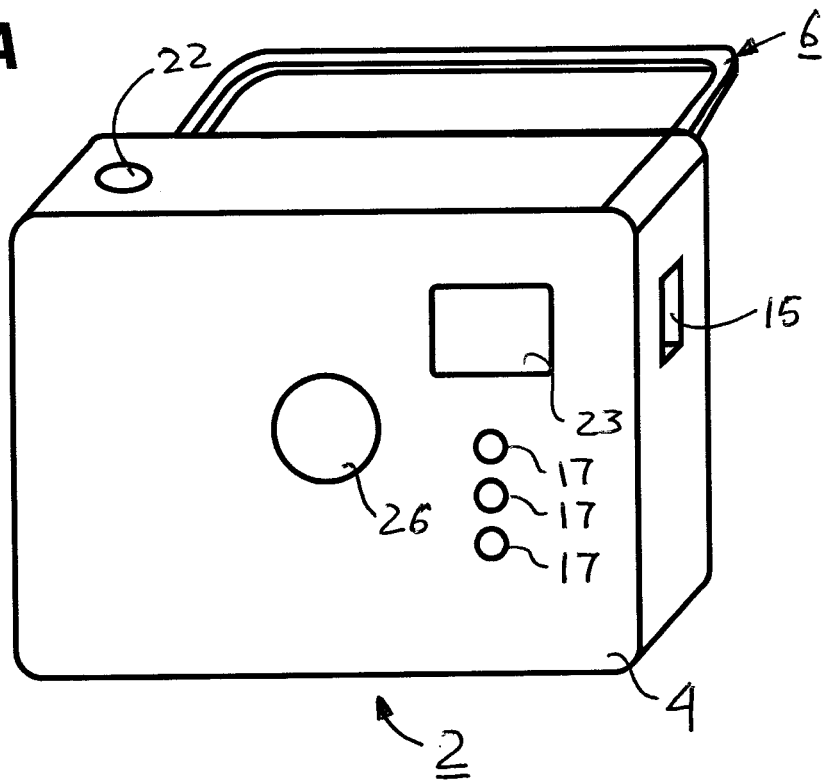
FIGS. 1A and 1B are perspective views of the back of the two embodiments of the present invention.
Figure 1B:
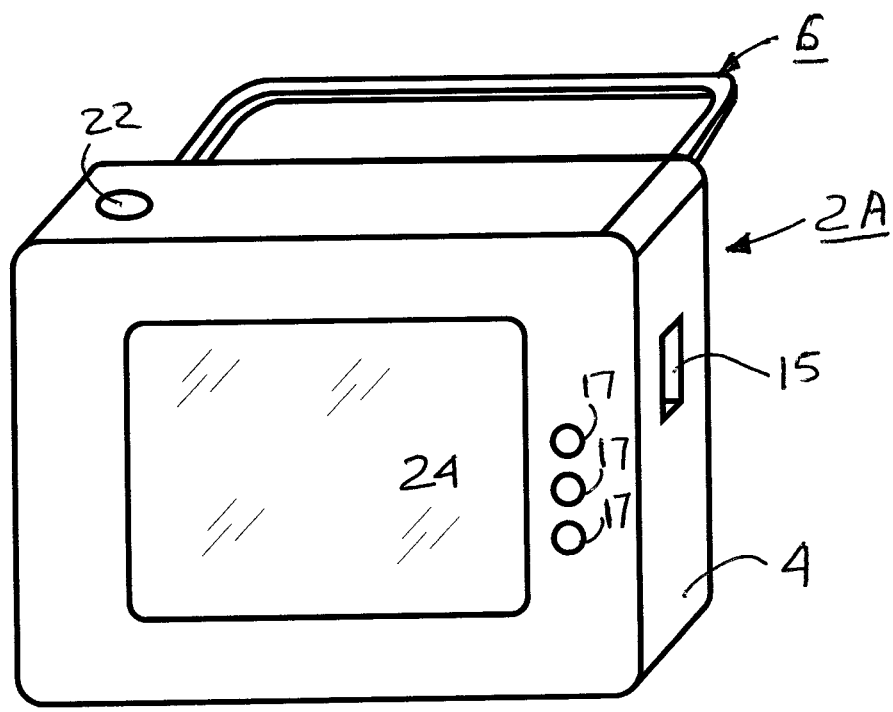
Figure 2:
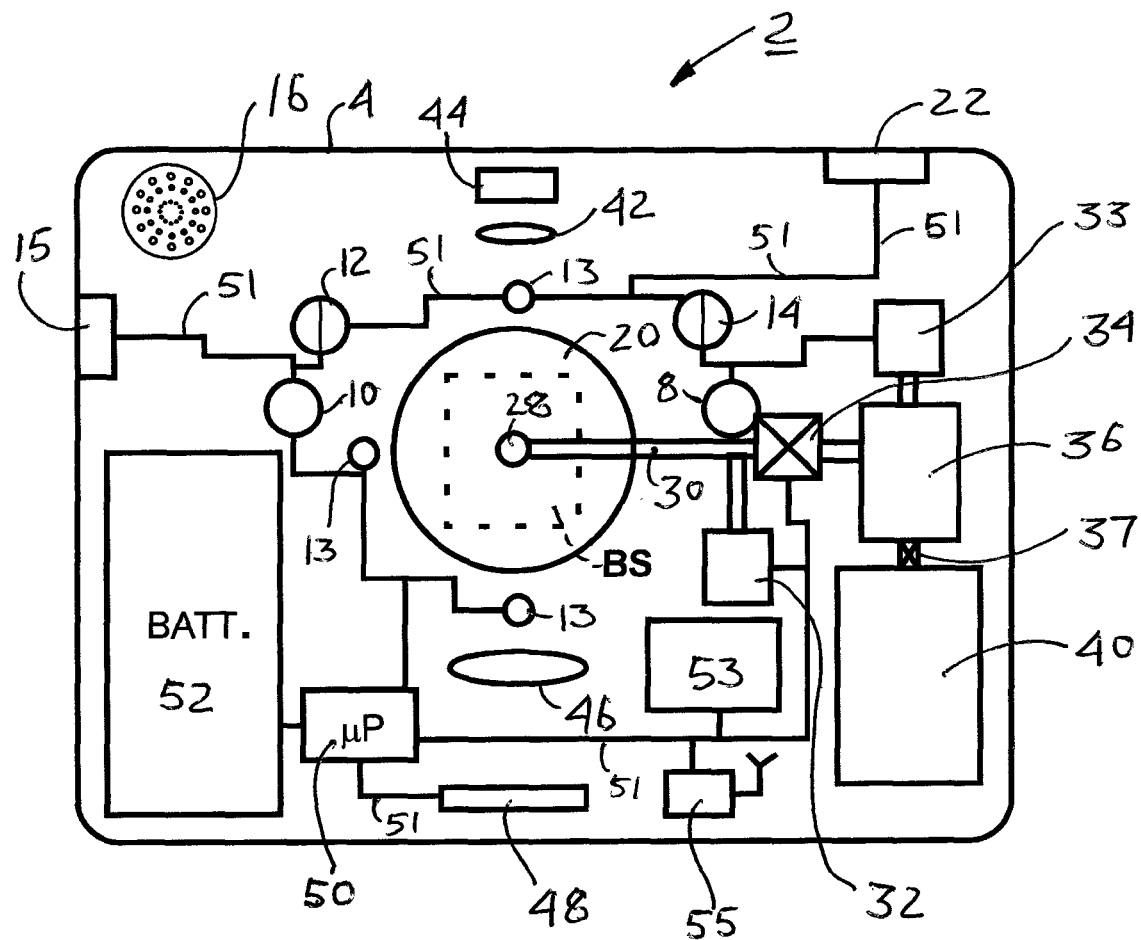
FIG. 2 is a partial sectional view along cross sectional line A-A of the FIG. 1.

As shown on FIGS. 1, 1A and 1B prior to measurement an optional forehead rest assembly 6 which is normally stored in housing 4 is folded out. The use of the forehead rest helps to position tonometer at proper distance to subject's eye by steadying tonometer, but it is not mandatory, since the proper distance is automatically indexed when the subject brings the gaze target into focus.

Figure 1C:
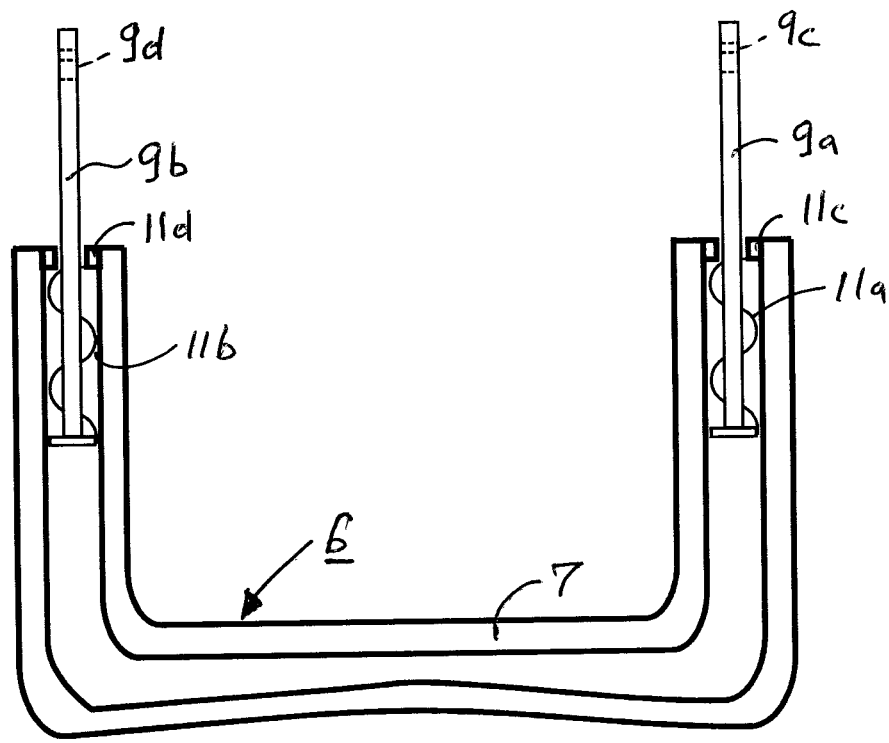
FIG. 1C is cross section of forehead rest assembly.
Figure 1D:
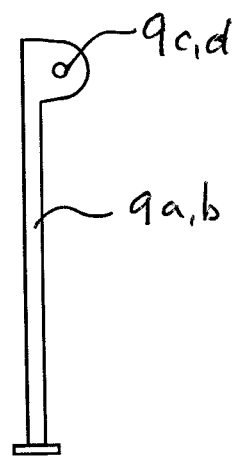
FIG. 1D is a side member of forehead rest assembly.

FIG. 1C shows forehead rest assembly 6 which consists of an essentially U-shaped main member 7 which interacts with two side members 9a and 9b which are spring loaded and can retract into the side sections of the main member 7. Side members 9a and 9b are biased by springs 11a and 11b respectively. The travel of side members 9a and 9b is limited by internal stops 11c and 11d in the main member 7. As shown on FIG. 10 side members 9a and 9b have transverse openings 9c and 9d respectively which enable forehead rest assembly 6 to pivot for storage around corresponding pins (not shown) in housing 4.

Figure 5:
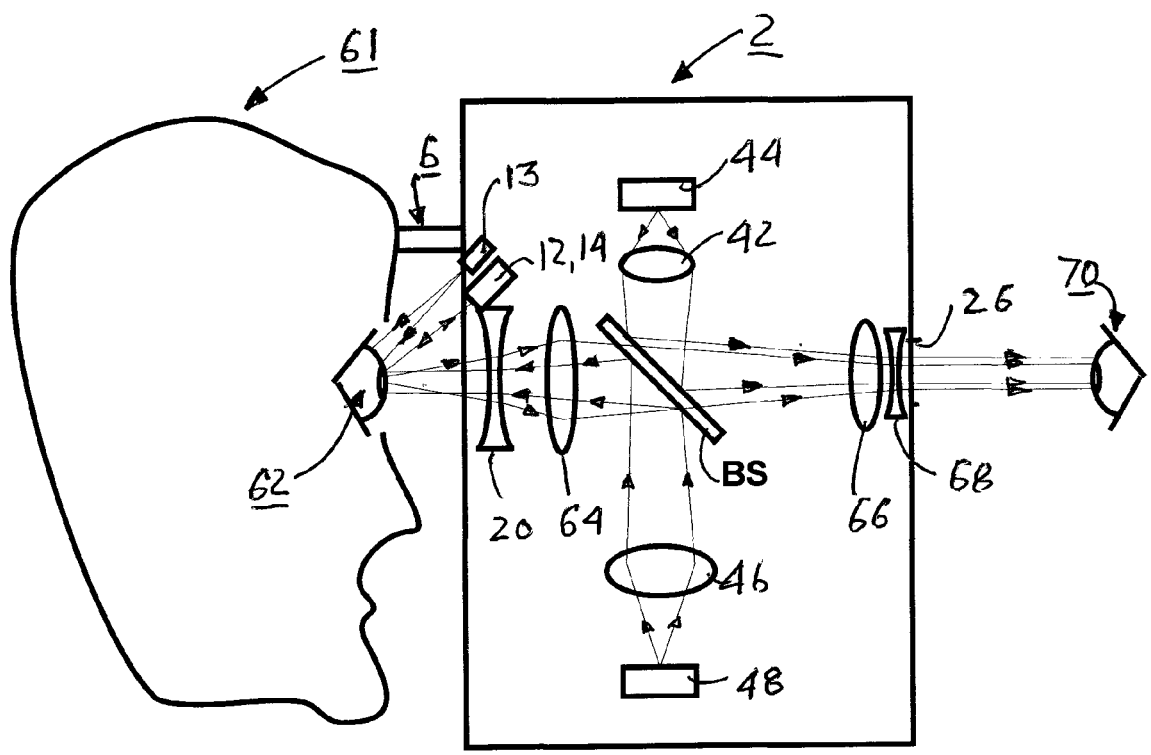
FIG. 5 is a partial sectional view along cross sectional line B-B of the FIG. 1 omitting some elements for clarity.

The subject himself or an operator positions tonometer 2 so rest 6 is against subject's forehead 61 opposite one of his eyes 62 as shown on FIG. 5.

Figure 7:
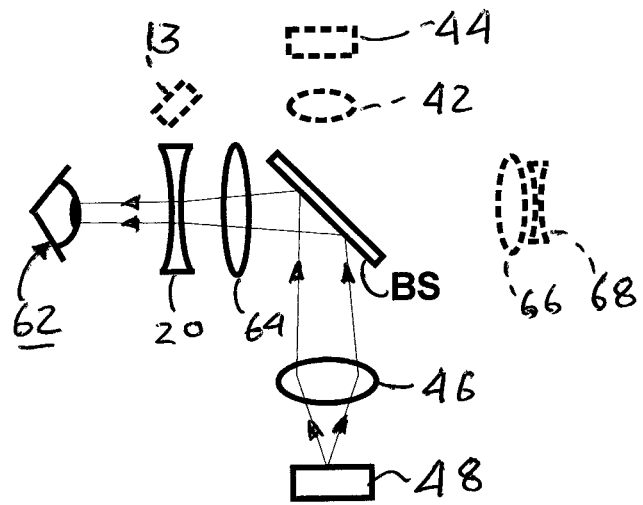
FIG. 7 is a simplified schematic of the optical train for the alignment target imaging for viewing by subject in FIG. 5.

Referring to FIGS. 2, 5 and 7 gaze target 48 is turned on and is imaged for observation by the subject via lens element 46, beamsplitter BS and lens system elements 20 and 64. The combined effect of these lens systems is to provide a narrow-angle view of target 48 which necessitates proper alignment of the subject's eye in order for him to see the target well. The optical design of these lens systems ensures a sufficient depth of field so that subject's eye is able to accommodate the shift in the position of the tonometer when it is moved to and from subject's eye for proper distance for measurement.

Target 48 is preferably a small electronic display, which is preferably a back-lighted liquid crystal (LCD), and can be monochromatic or color. Alternatively, target 48 can be of a light-emitting type, such as light-emitting diodes (LED), plasma, or electroluminescent. The preliminary eye alignment is achieved by animating or moving the target image to attract and hold subject's attention, and bring him to gaze at the target along the optical axis of the target imaging system which by design coincides with the optical axis of the tonometer.

Figure 15:
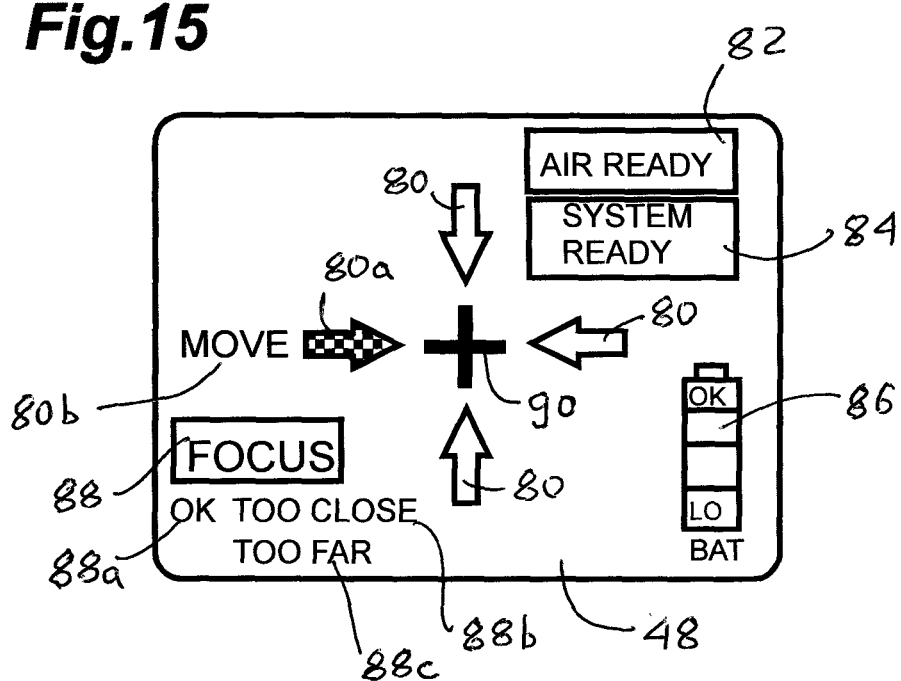
FIG. 15 is a sample display of the gaze target, eye alignment and system status.

Referring to FIG. 7 when tonometer operation is selected for conduct by the subject himself, target 48 includes in addition to the central gaze target, a system status and alignment information. An example of such target display is shown on FIG. 15. Central gaze target 90 is represented as a crosshair, but can be any image, stationary or animated, suitable for acquiring and retaining subject's attention. Alignment indicators 80 display alignment of subject's eye with respect to tonometer optical axis and show the needed correction when re-alignment is needed by changing their color like 80a, shape, blinking or a message similar to 80b. Focus status is indicated by message 88 and status indicators 88a, 88b, and 88c. When tonometer is out of focus, message 88 and corresponding status indicator 88a or 88b may be made to blink, change color or shape. Simultaneously, audio instructions for alignment and/or sounds accompanying any central target 48 animation can be produced by audio enunciator 16 under control of microprocessor 50. System status indicators such as air supply readiness 82, overall system readiness 84 and battery charge level 86 are included in the display.

For operator-assisted measurement, subject's eye 62 is illuminated for viewing by light sources 13 positioned around lens element 20.

Figure 6:
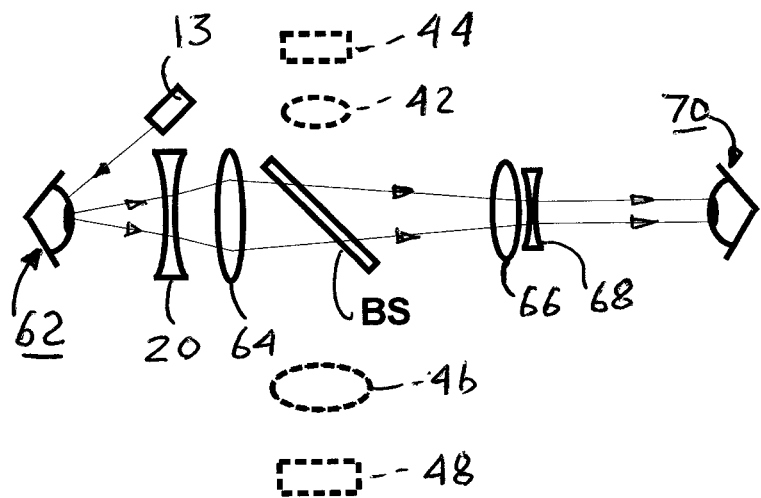
FIG. 6 is a simplified schematic of the optical train for the subject's eye observation by operator in FIG. 5

Referring to FIGS. 5 and 6 operator 70 observes subject's eye 62 via lens system elements 20, 64, beamsplitter BS and lens system elements 66 and 68.

Figure 8:
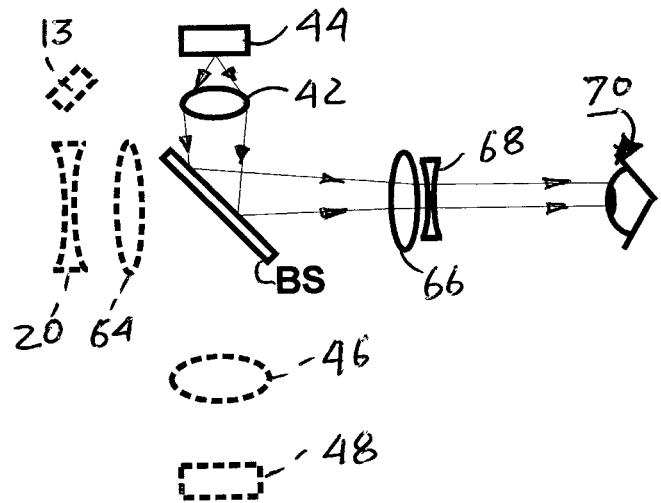
FIG. 8 is a simplified schematic of the optical train for the system status display for operator in FIG. 5.
Figure 16:
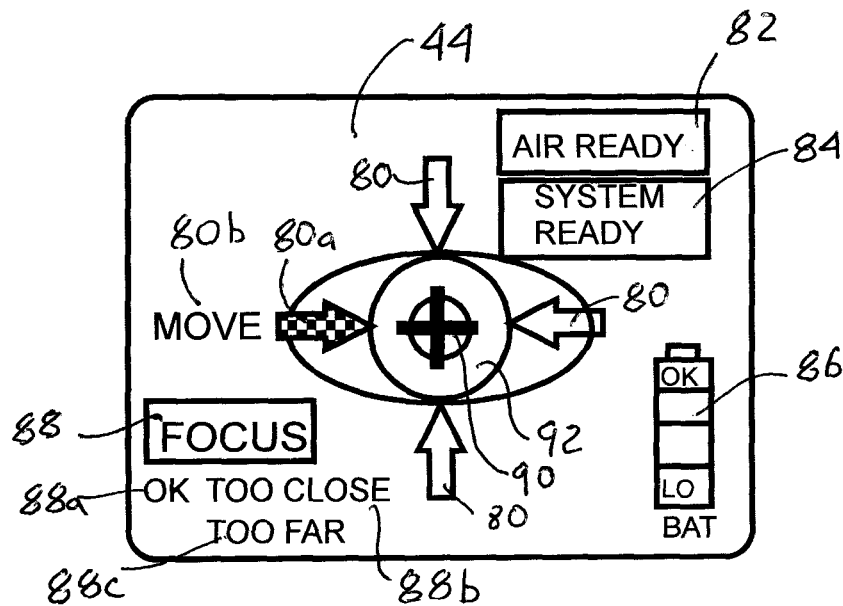
FIG. 16 is a sample of the system status, eye alignment display and system status including superimposed image of subject's eye.
Figure 17:
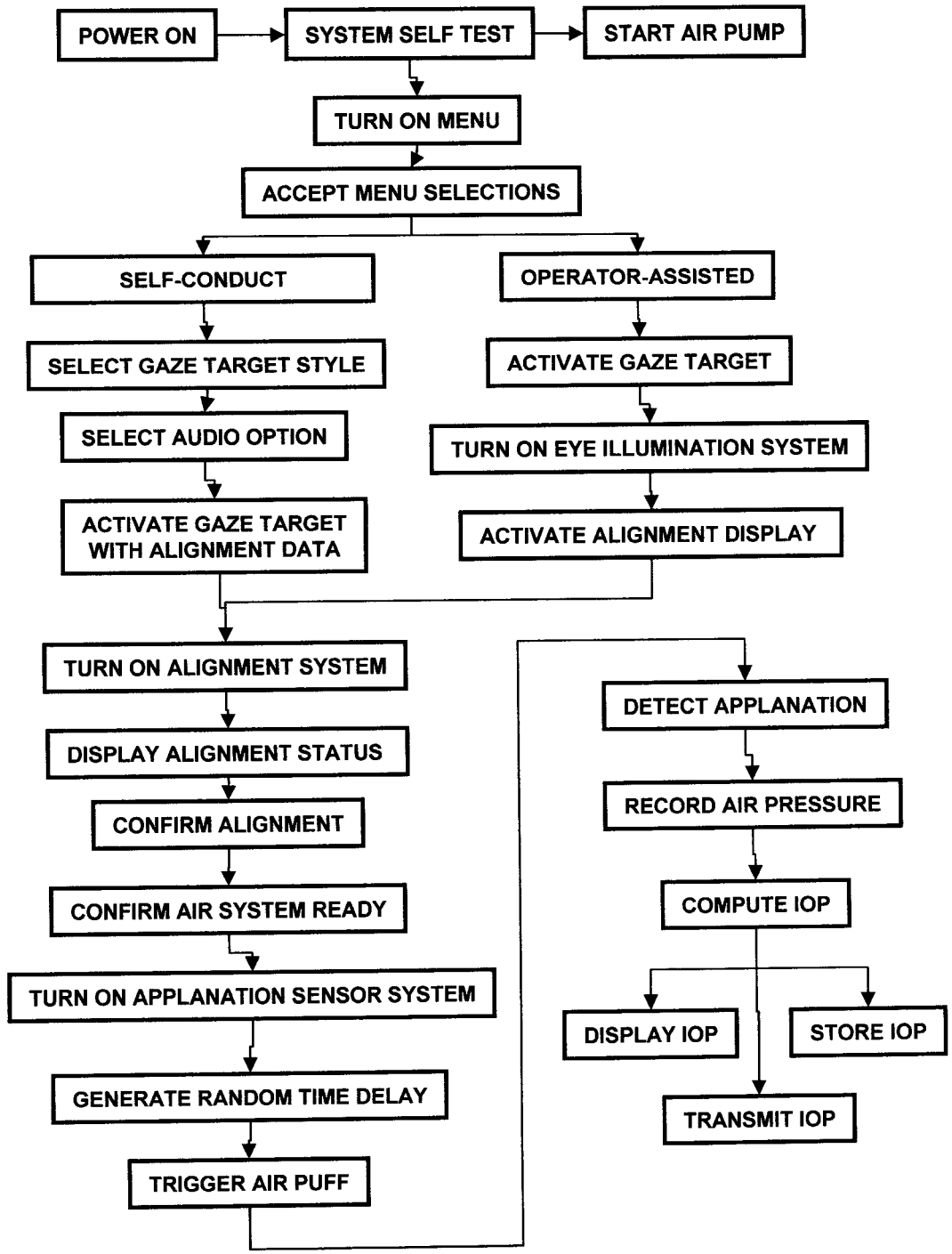
FIG. 17 is tonometer system's simplified operational sequence diagram.

Referring to FIGS. 5 and 8 system status including alignment information and guidance are displayed via system status display 44 which is made available for viewing by operator 70 via imaging sub-system consisting of lens element 42, beamsplitter BS and lens system elements 66 and 68. To facilitate operator's convenience, this and other system information is superimposed onto the image of subject's eye viewed by operator by the action of beamsplitter BS. An example of information display is shown on FIG. 16. In addition to the elements presented on FIG. 15 for the self-conducted measurement, the display 44 contains an image 92 of subject's eye 62 to assist with alignment process. Gaze target 90 representation can also be a combination of what subject sees and an additional superimposed alignment aid for the operator. For example, target 48 which is visible to the subject can be replicated in display 44 visible to the operator, but displayed dimmed or of different color, with an overlay of a simpler alignment aid. This enables operator to monitor the target visible to the subject. This is advantageous for pediatric subjects when an operator may want to comment on what a child sees to guide him through the procedure.

Simultaneously, audio instructions and/or sounds accompanying target 48 animation can be produced by audio enunciator 16 under control of microprocessor 50.

The subject himself or operator then advances tonometer closer to the subject's eye by compressing forehead rest assembly 6 until the system determines that a proper focus is reached and commences the measurement. As mentioned earlier, using forehead rest is not mandatory, since the proper distance is automatically indexed when the gaze target is in focus for the subject.

Referring to FIGS. 2, 5 and 6 subject's eye alignment, including proper focus position is verified by microprocessor 50 via alignment sensors 12 and 14. These sensors each consist of the light source—detector pair known in the art and measure reflectance of the subject's eye.

IOP Measurement

As the subject's eye alignment, and air supply readiness are confirmed microprocessor 50 turns on the applanation detection system and, after a short random time interval opens valve 34 which releases compressed air from chamber 36 via plenum 30 to orifice 28 in lens systems 20 and 64 and ultimately toward subject's eye 62. Random time delay, while optional, improves the accuracy of the measurement by minimizing subject's squinting and other potential involuntary actions by making the exact air pulse timing unknown and preventing subject's conditioning to it. After the release of the air pulse, applanation detection ensues.

Figure 4:
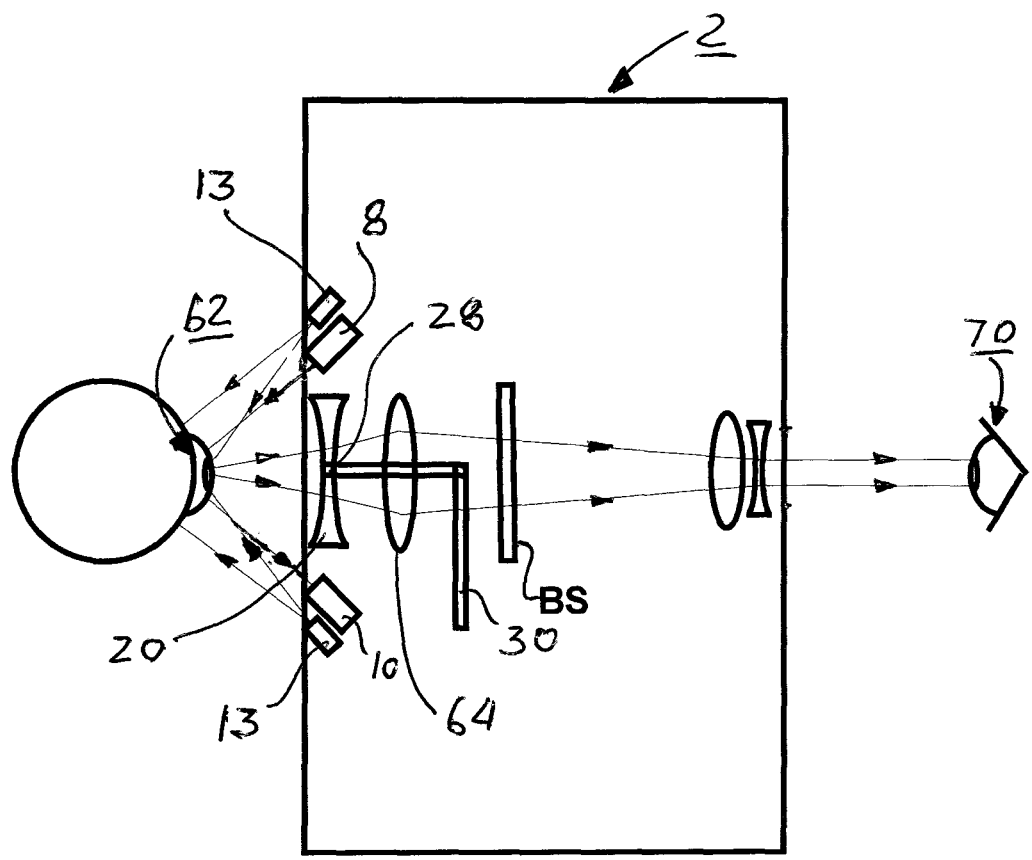
FIG. 4 is a partial sectional view along cross sectional line C-C of the FIG. 1

Referring to FIGS. 1, 2 and 4, subject's eye 62 is illuminated by applanation light probe source 8. Upon reflection from the cornea the light is detected by applanation detector system 10 which is preferably equipped with light collecting optical elements and an internal pinhole in front of a light sensor element which together comprise a corneal applanation detection mechanism well known in the art. As cornea flattens ("applanates") under the action of the air pulse, it reflects the light probe beam differently which is detected by the system.

Pressure sensor 32 measures air pressure inside plenum 30 while corneal applanation detection takes place. As soon as applanation is detected by light source 8—detector system 10 combination, output of sensor 32 is read by microprocessor 50 and the IOP value is subsequently calculated. The IOP value can then be displayed in several different ways, such as on the system status display 44, onto the target display 48, via an audio announcement by audio enunciator 16, a combination thereof, an auxiliary display 23, a bargraph type LED or LCD display, or discrete LEDs of different colors corresponding to the IOP value measured.

All alignment and applanation detection light sources preferably emit infra-red light invisible to the subject, so as not to distract him or cause discomfort. The eye illumination sources 13 and target 48 illumination source in this embodiment preferably emit visible light. IOP measurement data generated by microprocessor 50 can be transferred to other devices via a wired data port 15 or wirelessly via a wireless transceiver 55. The present preferred technology for the wired port is USB, while for the wireless port it is IEEE 802.11 also known as WiFi, or BlueTooth. All these data transport mechanisms are well known in their respective arts.

Additional Embodiments

In the foregoing description like components are labeled with like numerals.

An alternate tonometer embodiment 2A is shown on FIGS. 1B, 9, 10 and 11. In this embodiment operator's direct observation of the subject's eye and the corresponding optical system are replaced with internal electronic camera 74 with its corresponding imaging system and display 24.

Figure 9:
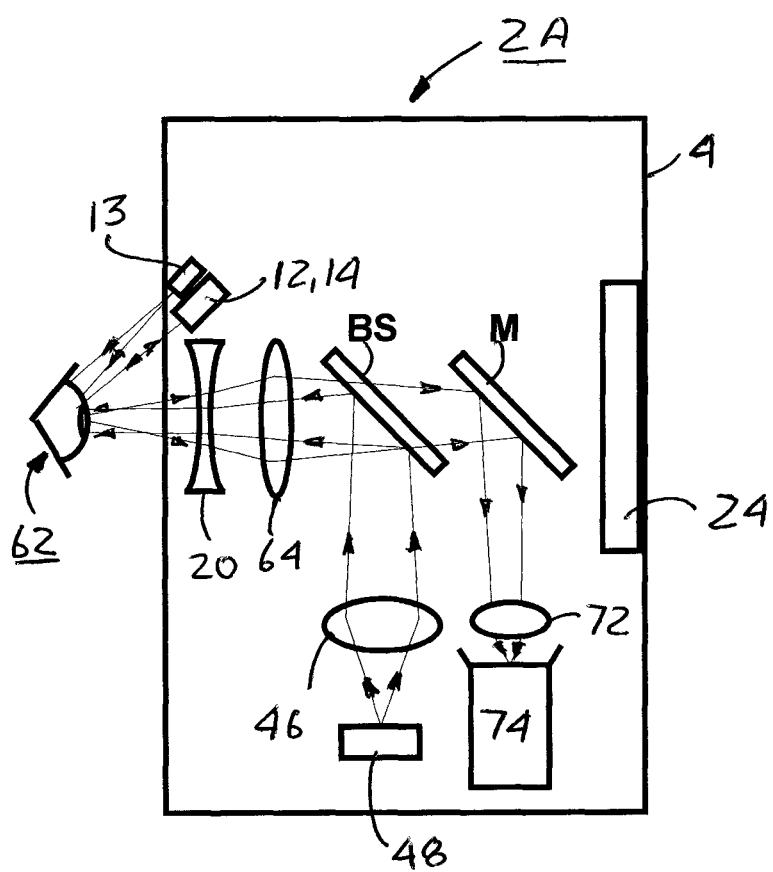
FIG. 9 is a partial sectional view similar to one in FIG. 5 but featuring alternative embodiment of FIG. 1B.
Figure 10:
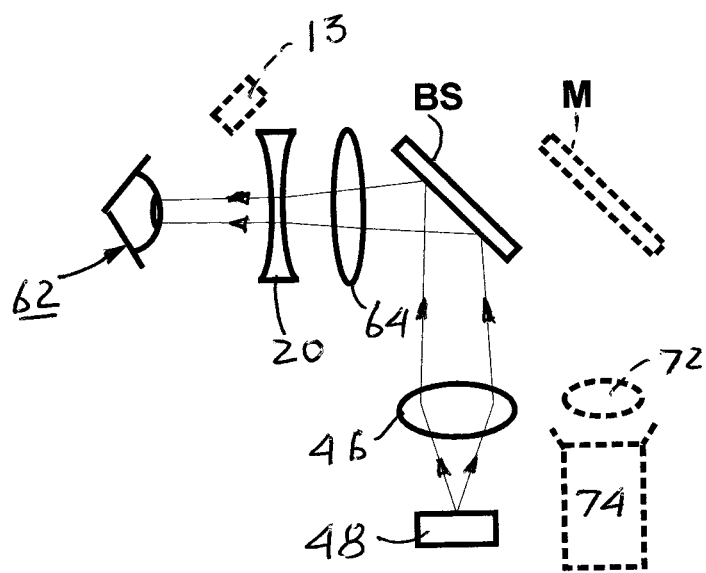
FIG. 10 is a simplified partial schematic of the optical system for viewing of the alignment target by subject in tonometer embodiment on FIG. 1B.

Referring to FIGS. 9 and 10 subject 61 with his eye 62 views gaze target 48 via an optical system consisting of imaging lens element 46, beamsplitter BS and lens system elements 20 and 64.

Figure 11:
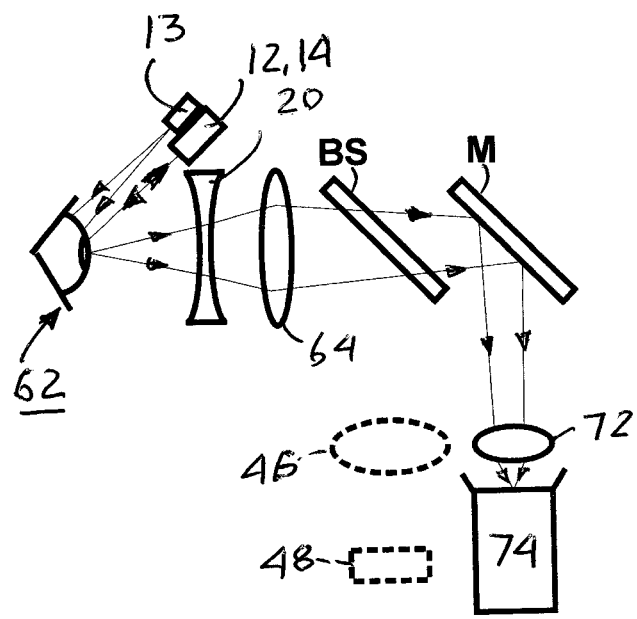
FIG. 11 is a simplified partial schematic of the optical system for imaging of the subject's eye for the camera in tonometer embodiment on FIG. 1B.

Referring to FIGS. 9 and 11 subject's eye 62 is illuminated by illuminators 13 while its precise alignment to the tonometer optical axis is monitored by alignment detectors 12 and 14. Subject's eye 62 is imaged via beamsplitter BS, turning mirror M and imaging lens 72 onto camera 74. The output of camera 74 and any additional information, such as alignment status and guidance, system status and the resulting IOP value are then displayed on display 24.

It is also possible to detect corneal applanation with this camera by illuminating the eye with one or more narrow beam light sources and capturing their reflection(s) from the cornea.

Figure 12:
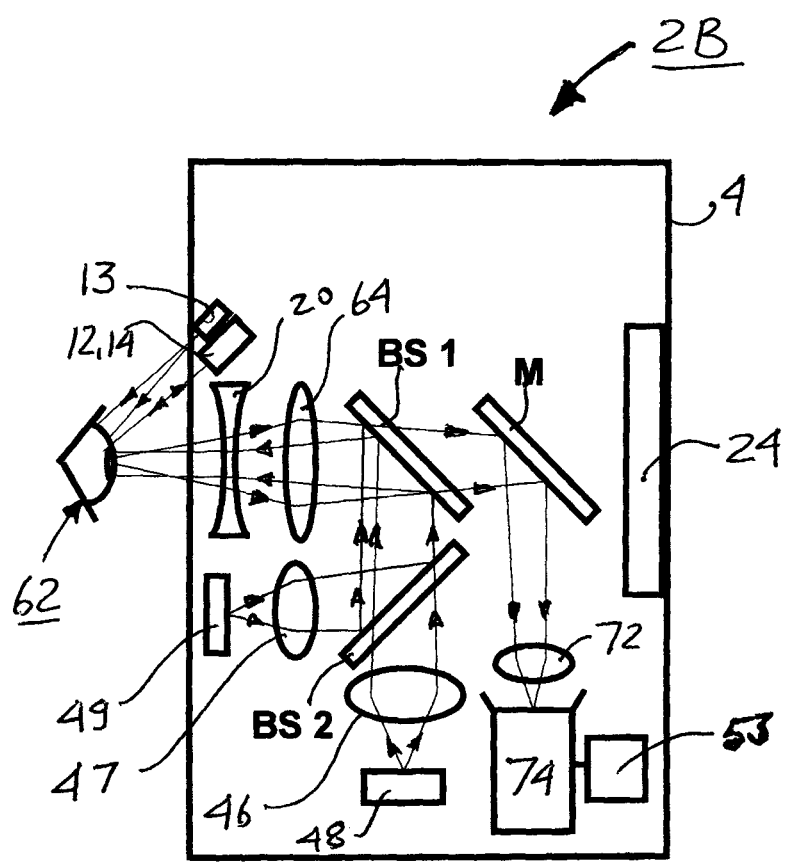
FIG. 12 is a partial sectional view similar to one in FIG. 5 but featuring alternative tonometer embodiment with cornea 3-D shape measurement feature.
Figure 13:
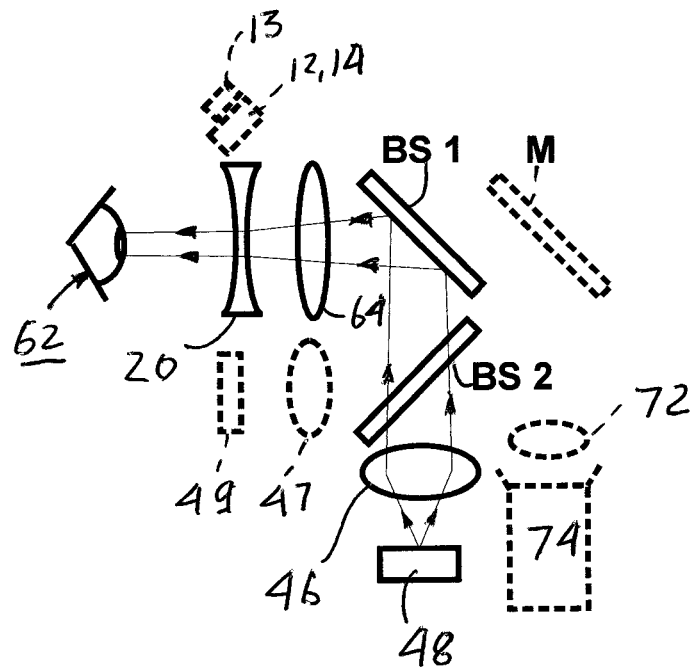
FIG. 13 is a simplified partial schematic of the optical system for viewing of the alignment target by subject in tonometer embodiment on FIG. 12.
Figure 14:
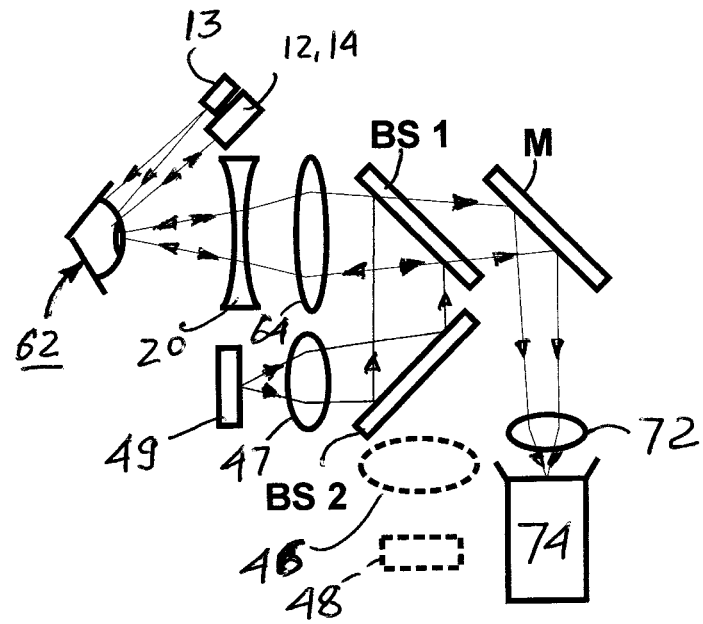
FIG. 14 is a simplified partial schematic of the optical system for the cornea shape target projection and subject's eye imaging in embodiment on FIG. 12.

Another tonometer embodiment 2B based a cornea shape calculation function is shown schematically on FIG. 12. In this embodiment optical element 47 images target 49 onto subject's eye 62 via beamsplitters BS1 and BS2. Target 49 is made to display a cornea test pattern consisting of concentric light and dark rings, which is well known in the art for cornea shape measurement. Alternatively, a rectangular grid-, a multiple dot-, or other patterns can be displayed. Target 49 is preferably a back-lighted LCD, with its illumination source preferably infra-red, rather than visible, or it can be a static transmission mask with a backlight source. The image of this pattern on subject's cornea is conveyed to camera 74 via lens system elements 20 and 64, beamsplitter BS1, turning mirror M and imaging lens 72. Illuminators 13 can be temporarily turned off for the camera to acquire image of only the test pattern on the cornea. The resulting image output from the camera is then captured by image processor 53 which can be a stand-alone device or an internal implementation of microprocessor 50 or camera 74 itself. By processing the image, a 3-dimensional map of the cornea is generated. If target 49 illuminator is made to emit infra-red light rather than visible, beamsplitter BS2 can be replaced by a dichroic mirror. If eye illuminator sources 13 are also infra-red, camera 74 has to be sensitive only to infrared light.

The cornea shape measurement feature can be used to measure the IOP without the need for a dedicated cornea applanation detection system. According to this method, cornea shape is measured at least twice: just before, and also during the air pulse, and the differences between the two computed shapes are compared and correlated to the air pressure. Several shape measurements can be made during the duration of the air pulse for better data correlation. Due to high sensitivity of this method very small cornea shape change can be detected, thus requiring a much weaker air pulse pressure. As a result, the measurement can be made more comfortable for subjects. Also, by correlating localized cornea shape changes versus air pressure, additional cornea qualities can be measured as well, such as cornea elasticity versus air pressure, and also distribution of elastic non-uniformities throughout cornea which may indicate underlying localized cornea defects. Thus, non-uniform thinning of the cornea, such as in keratoconus and other corneal diseases can be detected.

Additionally, an interferometric or Moiré technique can also be utilized for comparing the cornea shape before and during the air puff and subsequently analyzing them. These methods, also being quite sensitive, would require a lower air puff pressure needed to deform the cornea with the corresponding decrease in patient discomfort.

For all embodiments of the instant invention alternative air compression methods can be utilized, such as solenoid- or spring-activated plungers. Solenoids can be of linear- or rotational types which are well known the art. With such solenoids used for an air drive, accumulation chamber can be eliminated. The drawbacks in using solenoids are their relatively slow activation speed, high power surge requirements, and potential for increased operational noise. Spring-loaded plungers are also known in the art, but require electronic trigger.

Although descriptions provided above contain many specific details, they should not be construed as limiting the scope of the present invention. Thus, the scope of this invention should be determined from the appended claims and their legal equivalents.

I claim:

1. A portable non-contact tonometer for measuring intra-ocular pressure of an eye of a subject comprising:
    a case;
    a liquid pulse generator;
    an orifice for delivering said liquid pulse onto a cornea of said subject, said orifice being in communication with said liquid pulse generator via a liquid flow plenum; wherein said liquid pulse applanates a cornea of said subject;
    an eye alignment detector subsystem to detect an eye position of said subject;
    a cornea applanation detector subsystem for detecting a cornea applanation event of said subject;
    a liquid pulse pressure sensor to measure pressure of said liquid pulse;
    a microprocessor subsystem comprising microprocessor and memory, for control of said tonometer and for computation and reporting a value of said intra-ocular pressure;
    a gaze target, said gaze target displaying moving target images
    a gaze target imaging subsystem restricting visibility of said gaze target, wherein an optical axis of said eye and an optical axis of said tonometer are aligned when said subject focuses on said gaze target;
    wherein said microprocessor subsystem receives information from said eye alignment detector subsystem and said gaze target imaging subsystem to confirm alignment of the optical axes of said eye and said tonometer;
    wherein, upon confirming alignment of said optical axes, said microprocessor subsystem initiates a randomized time delay; and
    wherein said liquid pulse generator delivers said liquid pulse onto said cornea following said randomized time delay.

2. The tonometer of claim 1, further including an internal power source.

3. The tonometer of claim 1, wherein said eye alignment detector subsystem comprises at least one illuminator and at least one detector.

4. The tonometer of claim 1, wherein said liquid pulse generator comprises a pressure pump connected to a liquid accumulator reservoir, said reservoir connected to a liquid pulse release valve, said valve communicating with said orifice via said liquid flow plenum.

5. The tonometer of claim 1, wherein said liquid pulse generator comprises a solenoid-actuated plunger compressing said liquid inside a liquid accumulator reservoir, said reservoir connected to a liquid pulse release valve, said valve communicating with said orifice via said liquid flow plenum.

6. The tonometer of claim 1, wherein said liquid pulse generator comprises a manually-actuated plunger compressing said liquid inside a liquid accumulator reservoir, said reservoir connected to a liquid pulse release valve, said valve communicating with said orifice via said liquid flow plenum.

7. The tonometer of claim 1, further including an audio annunciation subsystem, said audio annunciation subsystem capable of audibly delivering one or more of the following:
    a. operational instructions for said tonometer;
    b. status of measurement of said intra-ocular pressure of said eye;
    c. value of said intra-ocular pressure of said eye;
    d. one or more results of comparing said value of said intra-ocular pressure to one or more pre-determined values;
    e. audio signals generally contributing to said eye remaining focused on said gaze target.

8. The tonometer of claim 1, further including a pivotally deployable forehead rest assembly.

9. The tonometer of claim 1, further including an imaging system for imaging said eye.

10. The tonometer of claim 1, further including at least one eye illumination source.

11. The tonometer of claim 1, further including a viewing port, said port enabling viewing said eye by an operator.

12. The tonometer of claim 1, further including a system status display, said display selectively made available for viewing by one or more of the following:
    a. said subject;
    b. an operator.

13. The tonometer of claim 1, further including a communications transceiver capable of transmitting values of said intra-ocular pressure and said tonometer and identification data of said subject to external systems and receiving data from external systems.

14. The transceiver of claim 13, wherein said communications transceiver is of wired type.

15. The transceiver of claim 13, wherein said communications transceiver is of wireless type.

16. A method of determining intra-ocular pressure of a subject using a tonometer, comprising the steps of:
    a. acquiring initial shape information of a cornea of said subject by:

i. displaying a moving gaze target image to attract a gaze of said subject and align an optical axis of said tonometer with an apex of said cornea,
ii. upon confirming alignment of said optical axis and said apex, illuminating said cornea by a reference optical waveform of known parameters,
iii. acquiring a modified optical waveform reflected by said cornea, and
iv. determining a difference between said reference optical waveform and said modified optical waveform;
b. computing an initial three-dimensional map of said cornea from said initial shape information;
c. storing said initial three-dimensional map of said cornea in a first memory device;
d. applying a liquid pulse onto said cornea;
e. measuring air pressure of said liquid pulse at at least one time interval;
f. acquiring subsequent shape information of said cornea concurrently with said liquid pulse, and at at least one time interval, by:
i. displaying a moving gaze target image to attract a gaze of said subject and align an optical axis of said tonometer with an apex of said cornea,
ii. upon confirming alignment of said optical axis and said apex, illuminating said cornea by a reference optical waveform of known parameters,
iii. acquiring a modified optical waveform reflected by said cornea, and
iv. determining a difference between said reference optical waveform and said modified optical waveform;
g. computing a subsequent three-dimensional map of said cornea from said subsequent shape information;
h. storing said subsequent three-dimensional map of said cornea in a second memory device;
i. retrieving said initial three-dimensional map of said cornea from said first memory device;
j. retrieving said subsequent three-dimensional map of said cornea from said second memory device;
k. calculating a difference value from said initial three-dimensional map of said cornea and at least one said subsequent three-dimensional map of said cornea;
l. correlating said difference value to said liquid pulse pressure for at least one said time interval to derive said intra-ocular pressure.

17. The method of determining intra-ocular pressure of claim 16 wherein said reference optical waveform comprises plurality of spatial optical wave features, and
wherein said modified optical waveform comprises plurality of spatial optical wave features.

18. A portable non-contact tonometer for determining intra-ocular pressure of an eye of a subject, comprising:
a case;
an eye alignment detecting subsystem;
a gaze target;
a reference optical waveform projecting subsystem;
a liquid pulse generator;
a liquid pulse pressure sensor;
a microprocessor subsystem;
a cornea image capture subsystem; and
a gaze target imaging subsystem;
wherein said gaze target displays moving target images to attract gaze of said eye of said subject;
wherein said gaze target imaging subsystem restricts visibility of said gaze target, wherein an optical axis of said eye and an optical axis of said tonometer are aligned when said subject focuses on said gaze target;
wherein said eye alignment detecting subsystem detects alignment of the optical axes of said eye and said tonometer;
wherein said reference optical waveform projecting subsystem projects a reference optical waveform onto a cornea of said eye;
wherein said cornea image-capture subsystem acquires a first modified optical waveform reflected from said cornea;
wherein said microprocessor subsystem computes a first three-dimensional shape representation of said cornea using said reference optical waveform and said first modified optical waveform;
wherein, upon confirming alignment of said optical axes, said microprocessor subsystem initiates a randomized time delay;
wherein said liquid pulse generator subsequently applies liquid pulse onto said cornea to cause deformation of said cornea following said randomized time delay;
wherein said liquid pulse pressure sensor senses a pressure of said liquid pulse;
wherein said cornea image capture subsystem acquires a second modified optical waveform reflected from said cornea;
wherein said microprocessor subsystem computes a second three-dimensional shape representation of said cornea using said reference optical waveform and said second modified optical waveform;
wherein said microprocessor subsystem computes a difference between said first three-dimensional shape representation of said cornea and said second three-dimensional shape representation of said cornea;
wherein said microprocessor subsystem derives a value of said intra-ocular pressure by correlating said difference and said pressure of said liquid pulse;
wherein said reference optical waveform comprises plurality of spatial optical wave features; and
wherein said modified optical waveform comprises plurality of spatial optical wave features.

19. The tonometer of claim 18, further including:
an internal power source;
an automatic audio annunciation subsystem;
a display device;
a communications transceiver;
wherein said automatic audio annunciation subsystem is capable of audibly delivering one or more of the following:
a. operating instructions for said tonometer;
b. status of measurement of said intra-ocular pressure;
c. value of said intra-ocular pressure;
d. one or more results of comparing value of said intra-ocular pressure to one or more pre-determined values;
e. audio signals generally contributing to said eye staying focused on said gaze target, and
wherein said display device is capable of displaying said value of said intra-ocular pressure, and
wherein said display device is further capable of displaying operational status of said tonometer, and
wherein said communications transceiver is capable of transmitting values of said intra-ocular pressure to external systems and receiving data from external systems.

* * * * *